(12) United States Patent
Dreyfuss et al.

(10) Patent No.: US 9,888,997 B2
(45) Date of Patent: Feb. 13, 2018

(54) SOFT ANCHOR ASSEMBLY WITH BARBED FLEXIBLE STRAND AND TECHNIQUES FOR USE

(71) Applicant: Arthrex, Inc., Naples, FL (US)

(72) Inventors: Peter J. Dreyfuss, Naples, FL (US); E. Lyle Cain, Jr., Birmingham, AL (US); William T. Pennington, Mequon, WI (US); Paul C. Brady, Knoxville, TN (US)

(73) Assignee: Arthrex, Inc., Naples, FL (US)

( * ) Notice: Subject to any disclaimer, the term of this patent is extended or adjusted under 35 U.S.C. 154(b) by 323 days.

(21) Appl. No.: 14/803,187

(22) Filed: Jul. 20, 2015

(65) Prior Publication Data
US 2017/0020655 A1    Jan. 26, 2017

(51) Int. Cl.
| | | |
|---|---|---|
| *A61B 17/04* | (2006.01) | |
| *A61F 2/08* | (2006.01) | |
| *A61B 17/06* | (2006.01) | |
| *A61B 17/00* | (2006.01) | |
| *A61B 17/11* | (2006.01) | |

(52) U.S. Cl.
CPC ........ *A61F 2/0811* (2013.01); *A61B 17/0401* (2013.01); *A61B 17/06166* (2013.01); *A61B 2017/00862* (2013.01); *A61B 2017/0406* (2013.01); *A61B 2017/0412* (2013.01); *A61B 2017/0445* (2013.01); *A61B 2017/0464* (2013.01); *A61B 2017/06176* (2013.01); *A61B 2017/06185* (2013.01); *A61B 2017/1142* (2013.01); *A61F 2002/0817* (2013.01); *A61F 2002/0852* (2013.01); *A61F 2002/0888* (2013.01)

(58) Field of Classification Search
CPC .......... A61B 17/0401; A61B 17/06166; A61B 2017/0406; A61B 2017/0412; A61F 2/0811

See application file for complete search history.

(56) References Cited

U.S. PATENT DOCUMENTS

| | | | |
|---|---|---|---|
| 3,123,077 A | 3/1964 | Alcamo | |
| 3,981,051 A | 9/1976 | Brumlik | |
| 5,053,047 A * | 10/1991 | Yoon | A61B 17/0469 606/223 |
| 5,342,376 A | 8/1994 | Ruff | |
| 5,645,568 A | 7/1997 | Chervitz et al. | |
| 5,683,417 A | 11/1997 | Cooper | |
| 5,699,657 A | 12/1997 | Paulson | |
| 5,989,252 A | 11/1999 | Fumex | |
| 6,056,778 A | 5/2000 | Grafton et al. | |
| 6,083,244 A * | 7/2000 | Lubbers | A61B 17/0401 606/232 |
| 6,296,659 B1 | 10/2001 | Foerster | |
| 6,511,498 B1 | 1/2003 | Fumex | |
| 6,599,310 B2 | 7/2003 | Leung et al. | |

(Continued)

FOREIGN PATENT DOCUMENTS

| | | |
|---|---|---|
| CN | 203647403 | 6/2014 |
| EP | 2 724 673 A1 | 4/2014 |
| WO | WO 2006/079469 A1 | 8/2006 |

*Primary Examiner* — Ashley Fishback
(74) *Attorney, Agent, or Firm* — Blank Rome LLP

(57) ABSTRACT

A soft anchor assembly according to an exemplary aspect of the present disclosure includes, among other things, a sheath and a flexible strand at least partially surrounded by the sheath.

10 Claims, 5 Drawing Sheets

(56) References Cited

U.S. PATENT DOCUMENTS

| | | |
|---|---|---|
| 6,773,450 B2 | 8/2004 | Leung et al. |
| 7,285,124 B2 | 10/2007 | Foerster |
| 8,062,363 B2 | 11/2011 | Hirpara et al. |
| 8,679,157 B2 | 3/2014 | Stopek |
| 8,721,681 B2 | 5/2014 | Ruff et al. |
| 8,747,436 B2 | 6/2014 | Nawrocki et al. |
| 8,795,334 B2 | 8/2014 | Astorino et al. |
| 2007/0005110 A1 | 1/2007 | Collier et al. |
| 2007/0010857 A1 | 1/2007 | Sugimoto et al. |
| 2011/0046669 A1* | 2/2011 | Goraltchouk .... A61B 17/06166 606/228 |
| 2011/0048216 A1* | 3/2011 | Lindh, Sr. ........ A61B 17/06166 87/34 |
| 2011/0098727 A1 | 4/2011 | Kaiser et al. |
| 2011/0264141 A1 | 10/2011 | Denham et al. |
| 2012/0059417 A1 | 3/2012 | Norton et al. |
| 2012/0116450 A1 | 5/2012 | McDevitt et al. |
| 2012/0130406 A1 | 5/2012 | Odermatt et al. |
| 2012/0290004 A1 | 11/2012 | Lombardo et al. |
| 2013/0123810 A1 | 5/2013 | Brown et al. |
| 2014/0257379 A1* | 9/2014 | McClellan ....... A61B 17/06166 606/228 |
| 2014/0316460 A1 | 10/2014 | Graul et al. |
| 2015/0119907 A1 | 4/2015 | Fenton et al. |
| 2015/0157437 A1* | 6/2015 | Cohen ................. A61F 2/0063 606/151 |

\* cited by examiner

SOFT ANCHOR ASSEMBLY WITH BARBED FLEXIBLE STRAND AND TECHNIQUES FOR USE

BACKGROUND

This disclosure relates to a surgical device and methods of using the surgical device to attach body tissue, such as soft or hard tissue, to another piece of body tissue. More particularly, this disclosure is directed to a soft anchor assembly that includes a sheath and a barbed flexible strand at least partially extending through the sheath.

Orthopedic procedures are often performed to repair musculoskeletal injuries. For example, soft tissue may tear away from bone during vigorous exercise or sporting activities. When such tears occur, reattachment is often necessary to repair the damaged tissue. Suture anchors are one type of surgical device that has been developed to facilitate these repairs. Additional advancements in this field of technology are desired.

SUMMARY

A soft anchor assembly according to an exemplary aspect of the present disclosure includes, among other things, a sheath and a flexible strand at least partially surrounded by the sheath.

A soft anchor assembly according to another exemplary aspect of the present disclosure includes, among other things, at least one sheath and a flexible strand at least partially surrounded by the at least one sheath. The flexible strand includes a first plurality of barbs extending from the flexible strand.

A method according to another exemplary aspect of the present disclosure includes, among other things, attaching a first piece of body tissue to a second piece of body tissue. The attaching step includes the use of a soft anchor assembly having at least one sheath that at least partially surrounds a flexible strand having a first plurality of barbs allowing movement of the at least one sheath along said flexible strand in a first direction and restricting movement of the at least one sheath in a second direction.

A method according to another exemplary aspect of the present disclosure includes, among other things, attaching a first piece of body tissue to a second piece of body tissue. The attaching step includes engaging the first piece of body tissue with the flexible strand having a first plurality of barbs adjacent a first end and a second plurality of barbs adjacent a second end. The first end and the second end of the flexible strand are passed through at least one sheath.

DETAILED DESCRIPTION

This disclosure describes various soft anchor assemblies and associated surgical techniques for attaching body tissue to body tissue. The soft anchor assemblies are formed of "soft" materials, such as suture materials, that confer the ability to be inserted into bone sockets/holes and bunch together, collapse, expand and/or change shape to fixate within or adjacent the socket/hole. In some embodiments, the soft anchor assembly includes a sheath at least partially surrounding a flexible strand. In other embodiments, the soft anchor assembly includes multiple sheaths at least partially surrounding the flexible strand. The soft anchor assemblies of this disclosure may be utilized in various surgical techniques to attach body tissue to other body tissue. In the illustrated non-limiting embodiments, the body tissue could include soft or hard tissue. These and other features are described in greater detail in the following paragraphs of this detailed description.

Figure 1:
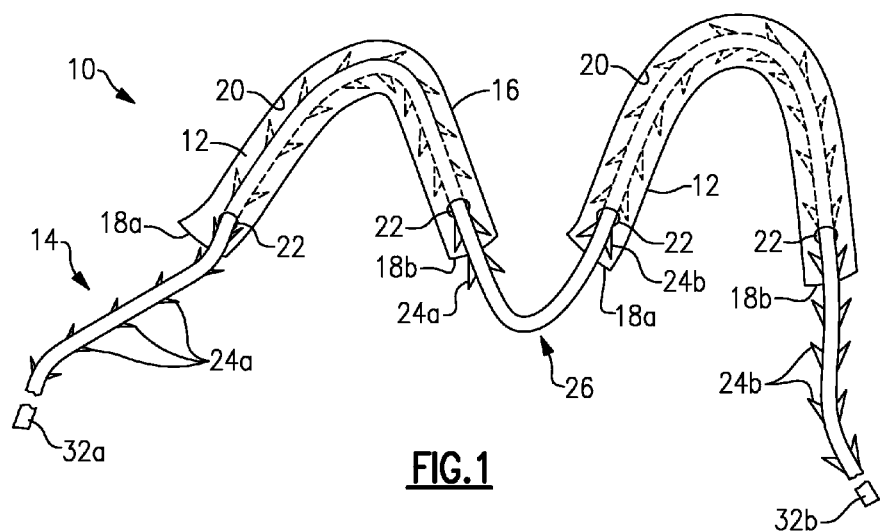
FIG. 1 illustrates a soft anchor assembly according to a first embodiment of this disclosure.

FIG. 1 illustrates a soft anchor assembly 10. The soft anchor assembly 10 is configured for use in various soft tissue repairs or fixations. For example, the soft anchor assembly 10 can be used in conjunction with a variety of orthopedic surgical repairs, including but not limited to rotator cuff repairs, Achilles tendon repairs, patellar tendon repairs, ACL/PCL reconstructions, hip and shoulder reconstructions, meniscal repairs, among many others.

In this disclosure, the soft anchor assembly 10 is referred to as a "soft" construct because it is formed of soft materials such as yarns, fibers, filaments, strings, fibrils, strands, sutures, etc., or any combination of such materials. The soft materials may be synthetic or natural materials, or combinations of synthetic and natural materials, and may be bio-degradable or non-degradable within the scope of this disclosure. In one non-limiting embodiment, the soft anchor assembly 10 is made exclusively of soft, suture-based materials.

The soft anchor assembly 10 may include at least two sheaths 12 and one flexible strand 14. The sheaths 12 include a tubular body 16 extending between opposing ends 18a, 18b. The opposing ends 18a, 18b may be open or closed ends. The tubular body 16 establishes a bore 20 that extends between the opposing ends 18a, 18b.

In one embodiment, the sheath 12 is a tubular sleeve made of a flexible material, such as a braided, woven, or knitted structure made of yarns, fibers, filaments, sutures or similar materials, or combinations of these materials. In another non-limiting embodiment, the sheath 12 is constructed of polyester suture material. Other materials may also be suitable to construct the sheath 12.

The flexible strand 14 is passed through at least a portion of the bore 20 of the sheath 12. The flexible strand 14 may assist in bunching together the sheaths 12 once the soft anchor assembly 10 is inserted at least partially into or through body tissue. In one embodiment, the flexible strand 14 passes through openings 22 formed through the tubular body 16. In the illustrated non-limiting embodiment, the openings 22 are spaced inward from the opposing ends 18a, 18b of the sheath 12. In another non-limiting embodiment, the openings 22 are located in the opposing ends 18a, 18b of the sheath 12. The flexible strand 14 may be of any length and includes a first end 32a and a second end 32b that extend outside of the sheath 12. This configuration can be used if the opposing ends 18a, 18b are open or closed ends.

In one embodiment, the flexible strand 14 is a suture and includes a first plurality of barbs 24a and a second plurality of barbs 24b separated by a central region 26 without any barbs. The first plurality of barbs 24a and the second plurality of barbs 24b extend in an inward direction such that the sheath 12 is allowed to move inward towards the central region 26 and restricted from moving outward toward a corresponding one of the first and second ends 32a, 32b. Although the first and second plurality of barbs 24a, 24b are shown on opposing axial sides of the flexible strand 14, the first and second plurality of barbs 24a, 24b could be located on only one side of the flexible strand 14, spiral around an exterior of the flexible strand 14, or be in another configuration on the exterior of the flexible strand 14.

Figure 2A:
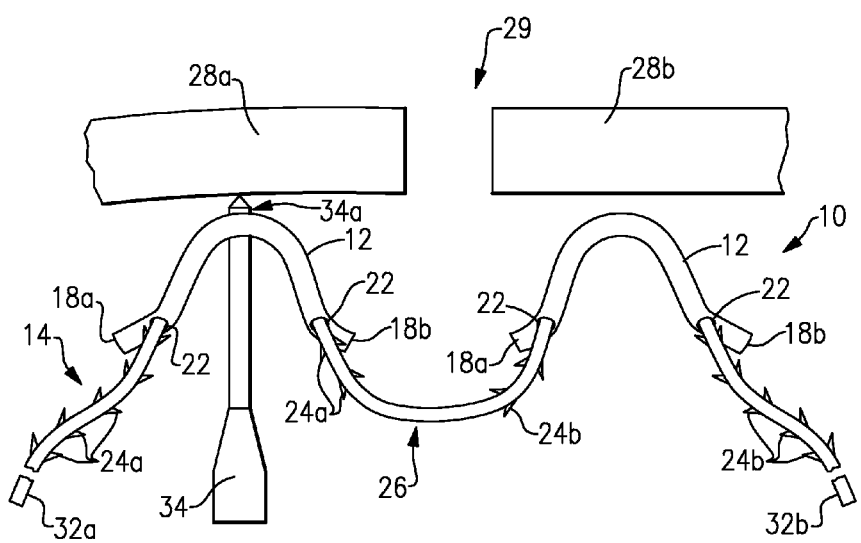
FIGS. 2A, 2B, and 2C illustrate a method of attaching pieces of body tissue using the soft anchor assembly according to the first embodiment of the disclosure.
Figure 2B:
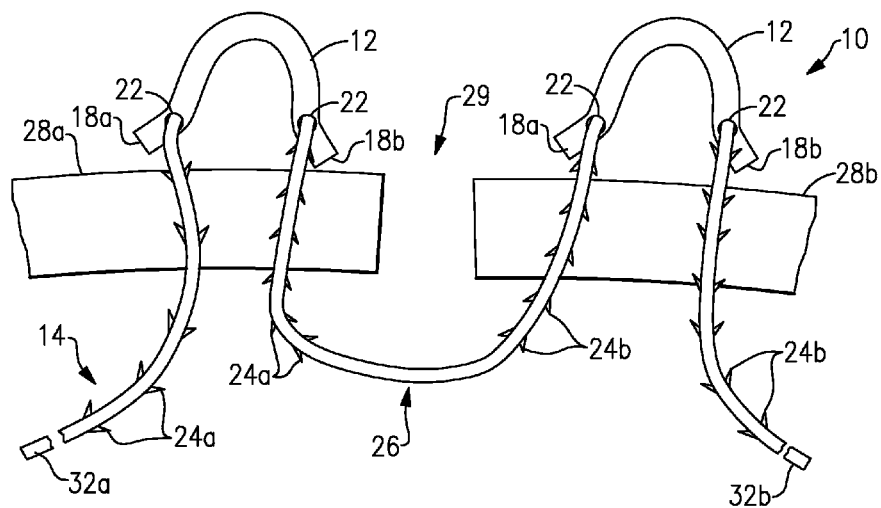
Figure 2C:
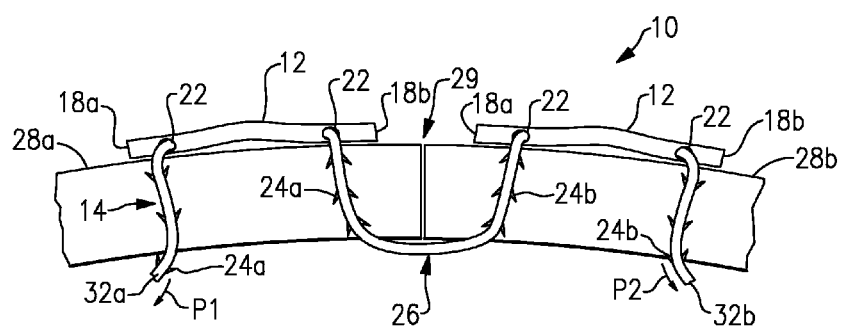

FIGS. 2A-2C schematically illustrate an exemplary method for attaching a first piece of body tissue 28a separated from a second piece of body tissue 28b by a tear 29 with the soft anchor assembly 10. Although the illustrated non-limiting embodiment shows the first and second pieces of body tissue 28a, 28b as being soft body tissue, the first and second pieces of body tissue 28a, 28b could also include a combination of soft tissue and hard tissue or two pieces of hard tissue. Additionally, the first piece of body tissue 28a and the second piece of body tissue 28b could part of a single piece of body tissue with the first and second pieces of body tissue 28a, 28b being portions of the single piece of body tissue located on opposite sides of the tear 29, such as with a torn meniscus.

First, as shown in FIG. 2A, the first piece of body tissue 28a is brought into relative close proximity with the second piece of body tissue 28b. One of the sheaths 12 surrounding the flexible strand 14 is placed within an opening 34a in a penetrating pusher tool 34 and aligned with the first piece of body tissue 28a. Once aligned with the first piece of body tissue 28a, the penetrating pusher tool 34 is passed through the first piece of body tissue 28a to locate the sheath 12 on an opposite side of the first piece of body tissue 28a. A similar procedure is followed with the penetrating pusher tool 34 to locate the other sheath 12 on an opposite side of the second piece of body tissue 28b.

The sheaths 12 surrounding the flexible strand 14 may be passed through the first and second pieces of body tissue 28a, 28b sequentially or simultaneously with the use of a second penetrating pusher tool 34 (not shown).

As shown in FIG. 2B, once the sheaths 12 have passed through a corresponding one of the first and second pieces of body tissue 28a, 28b, the flexible strand 14 is oriented with the central region 26 located in contact or in proximity to the tear 29 in the first and second pieces of body tissue 28a, 28b. The sheaths 12 are located on an opposite side of the first and second pieces of body tissue 28a, 28b from the central region 26 of the flexible strand 14.

As shown in FIG. 2C, the spacing between the tear 29 forming the first and second pieces of body tissue 28a, 28b is reduced by pulling the first end 32a of the flexible strand 14 relative to the first piece of body tissue 28a in the direction P1 and pulling the second end 32b of the flexible strand 14 relative to the second piece of body tissue 28b in the direction P2. Because the first and second plurality of barbs 24a, 24b angle inward, the first and second ends 32a and 32b of the flexible strand 14 are able to be pulled through the first and second piece of body tissue 28a, 28b, in the directions P1, P2. The first and second plurality of barbs 24a, 24b prevent the flexible strand 14 from retracting back through the first and second pieces of body tissue 28a, 28b once pulled in the directions P1 and P2, respectively.

Any excess length on the flexible strand 14 can be trimmed so that the first and second ends 32a, 32b of the flexible strand 14 would be flush with the first and second pieces of body tissue 28a, 28b, if desired. The first and second plurality of barbs 24a, 24b on the flexible stand 14 allow for knotless tissue fixation which would not be possible with the use of traditional barbless sutures.

Figure 3A:
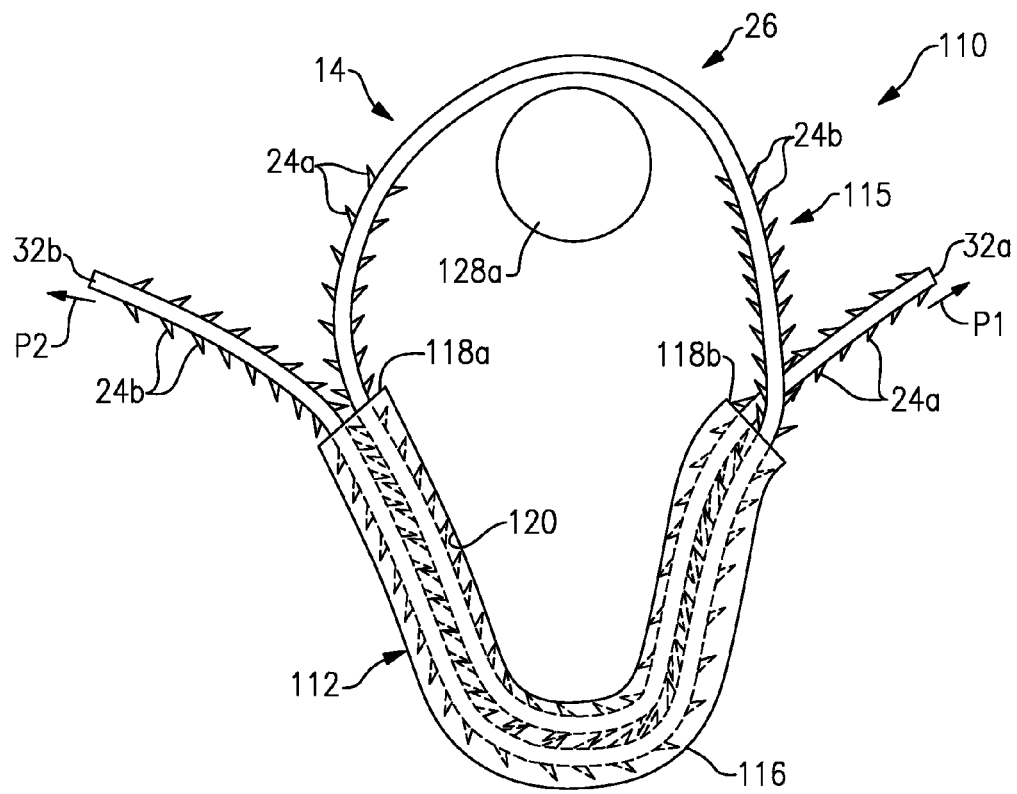
FIGS. 3A, 3B and 3C illustrate a soft anchor assembly according to a second embodiment of this disclosure and a method of attaching pieces of body tissue using the soft anchor assembly according to the second embodiment of the disclosure.
Figure 3B:
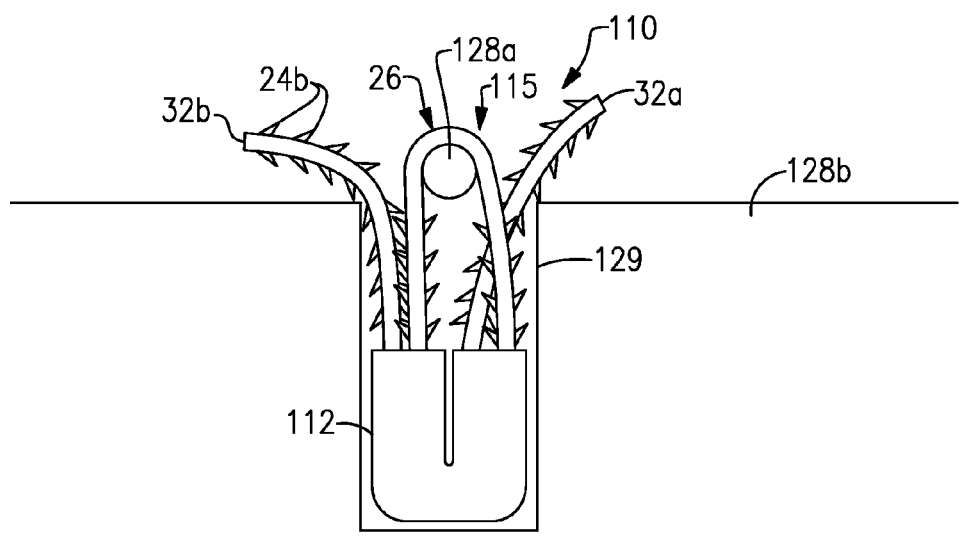

FIGS. 3A-3B illustrate a second non-limiting embodiment of a soft anchor assembly 110 that is similar to the soft anchor assembly 10 shown in FIG. 1 except as otherwise described below or shown in the Figures. The anchor assembly 110 includes at least one sheath 112 and the flexible strand 14 from the soft anchor assembly 10.

First, as shown in FIG. 3A, the flexible strand 14 is positioned relative to a first piece of body tissue 128a. In one non-limiting embodiment, the flexible strand 14 can wrap around the first piece of body tissue 128a such that an exterior of the flexible strand 14 contacts an exterior portion of the first piece of body tissue 128a as shown in FIG. 3A. In another non-limiting embodiment, the flexible strand 14 can be threaded through the first piece of body tissue 128a such that the central region 26 of the flexible strand 14 is aligned with the first piece of body tissue 128a. Alternatively, the central region 26 is spaced from the first piece of body tissue 128a and a portion of the flexible strand 14 including the first or second plurality of bards 24a, 24b is located within the first piece of body tissue 128a. In the illustrated non-limiting embodiment, the first piece of body tissue 128a is soft tissue and a second piece of body tissue 128b, shown in FIG. 3B, is hard tissue, such as bone.

The sheath 112 includes a tubular body 116 that extends between opposing ends 118a, 118b. The tubular body 116 establishes a bore 120 that extends between the opposing ends 118a, 118b. The opposing ends 118a, 118b of the sheath 112 are open to allow the flexible strand 14 to enter and exit the sheath 112 at the opposing ends 118a, 118b.

Once the flexible strand 14 has been positioned relative to the first piece of body tissue 128a, the first and second ends 32a, 32b of the flexible strand 14 are threaded through the openings in the opposing ends 118a, 118b in the sheath 112 such that the first plurality of barbs 24a overlap the second plurality of barbs 24b in the sheath 112. In another non-limiting embodiment, the first and second ends 32a, 32b of the flexible strand 14 are threaded through openings formed in the tubular body 116 spaced inward from the opposing ends 118a, 118b similar to the openings 22 in the sheath 12 shown in FIG. 1.

Because the first and second plurality of barbs 24a, 24b are both angled inward toward the central region 26, the first and second plurality of barbs 24a, 24b will slide past each other when the first and second ends 32a, 32b of the flexible strand 14 are pulled outward through the sheath 112. Pulling the first and second ends 32a, 32b of the flexible strand 14 in the directions P1, P2, respectively, will reduce the size of a loop 115 formed by the flexible strand 14. The first and second plurality of barbs 24a, 24b will restrict the loop 115 formed by the flexible strand 14 from expanding in size because the first and second plurality of barbs 24a, 24b will engage each other and restrict movement.

Referring to FIG. 3B, an opening 129 is formed in the second piece of body tissue 128b with a tool, such as a punch or a drill. The sheath 112 with the flexible strand 14 can then be placed within the opening 129 with a suitable tool to ensure that the sheath 112 and the flexible strand 14 are inserted in the opening 129. Inserting the sheath 112 and the flexible strand 14 in the opening 129 will secure the first piece of body tissue 128a relative to the second piece of body tissue 128b. Alternatively, the opening 129 is formed during insertion of the sheath 112 and the flexible strand 14 into the second piece of body tissue 128b.

Figure 3C:
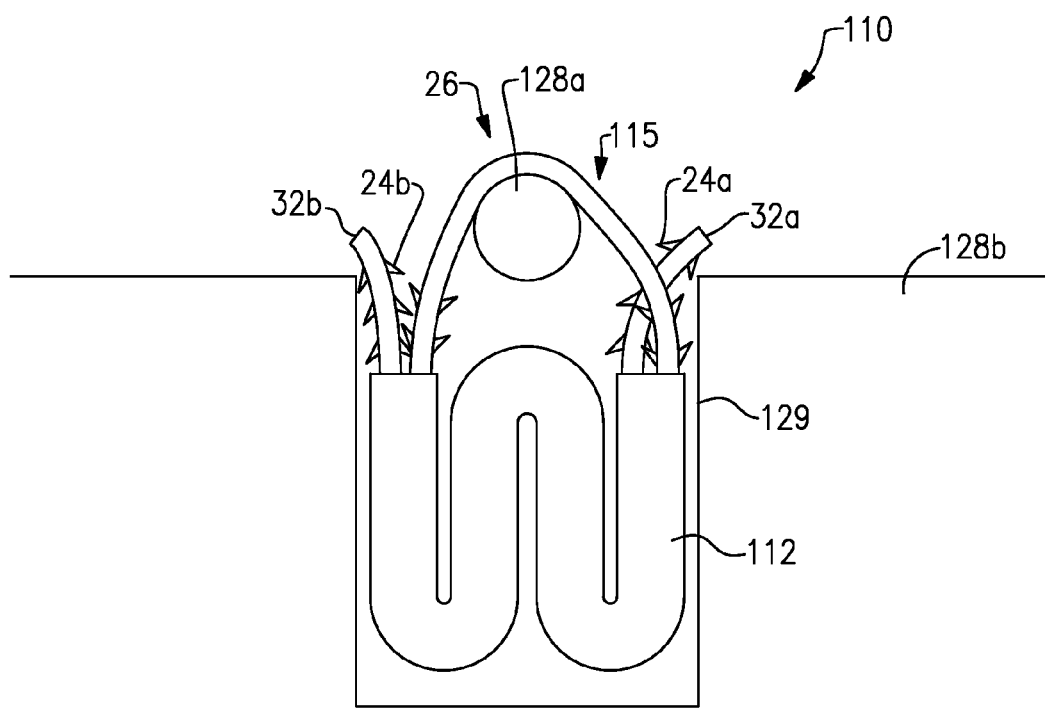

The first and second ends 32a, 32b of the flexible strand 14 are tensioned in the directions P1, P2, respectively, to lodge the anchor assembly 110 into the opening 129 to position the first piece of body tissue 128a relative to the second piece of body tissue 128b. The sheath 112 will bunch up and form a random pattern during lodging and/or tensioning, as shown in FIG. 3C. Any excess length on the flexible strand 14 can be trimmed to be flush with the second piece of body tissue 128b, if desired.

Figure 4A:
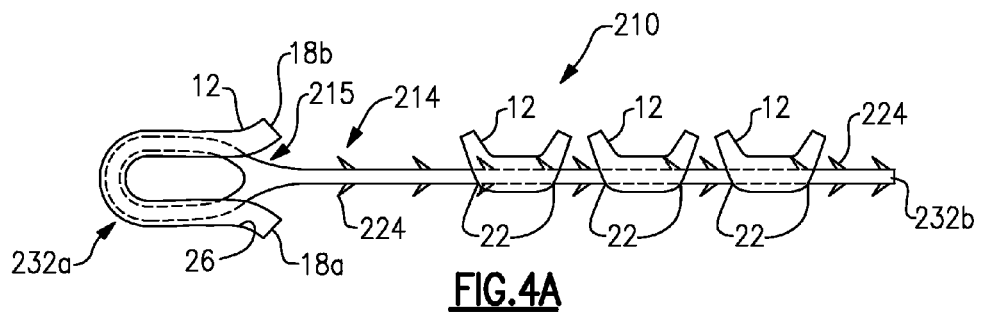
FIG. 4A illustrates a soft anchor assembly according to a third embodiment of this disclosure.
Figure 4B:
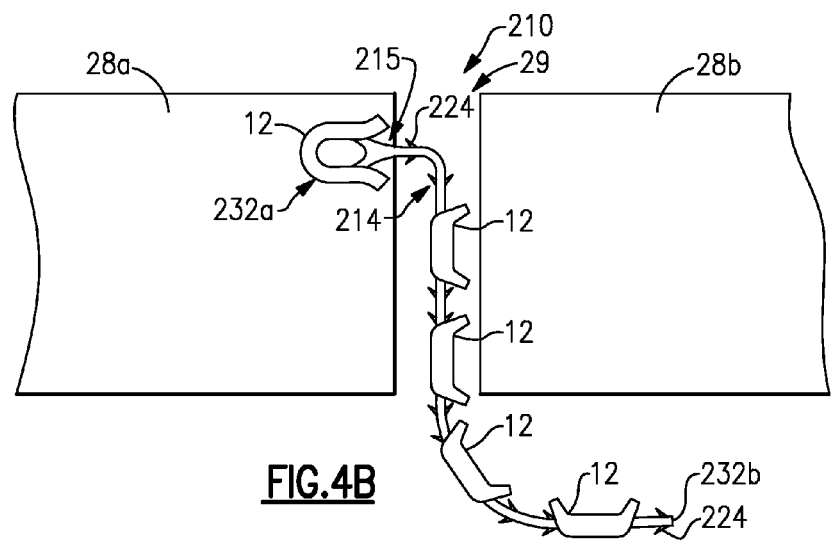
FIGS. 4B and 4C illustrate a method of attaching pieces of body tissue using the soft anchor assembly according to the third embodiment of the disclosure.
Figure 4C:
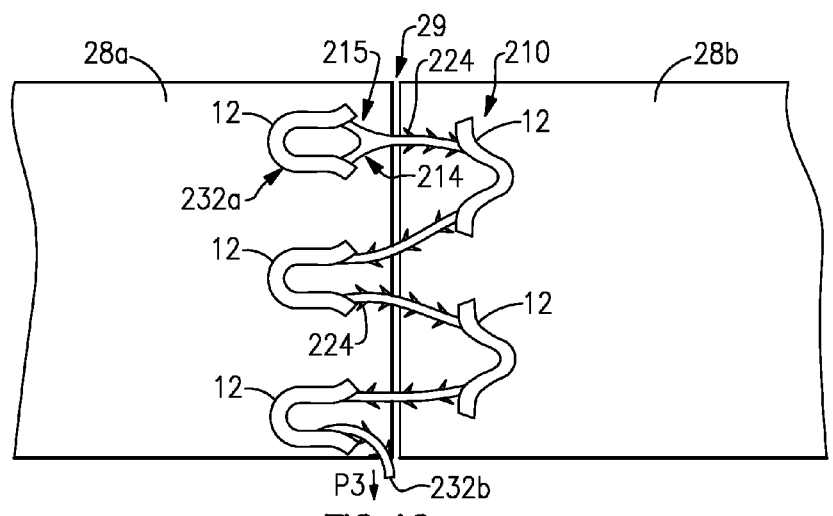

FIGS. 4A-4C illustrate yet another non-limiting embodiment of a soft anchor assembly 210 that is similar to the soft anchor assembly 10 shown in FIG. 1 except as otherwise described below or shown in the Figures. The anchor assembly 210 includes multiple sheaths 12 and a flexible strand 214.

The flexible strand 214 includes a loop 215 on a first end 232a passing through at least a portion of the bore 20 of the sheath 12. In order for the sheath 12 to be installed on the loop 215, the sheath 12 could be attached to the first end 232a of the flexible strand 214 before the loop 215 is formed. Alternatively, the sheath 12 could be separated along its axial length and then placed around the loop 215 and closed by stitching or another type of fastening, such as adhesive, depending on the material of the sheath 12, among other factors.

In one embodiment, the flexible strand 214 is a suture and includes barbs 224 extending along a length of the flexible strand 214 from the loop 215 to a second end 232b. The barbs 224 extend towards the loop 215 on the first end 232a. The barbs 224 allow each sheath 12 to slide along the flexible strand 214 from the second end 232b towards to loop 215 on the first end 232a and restrict each sheath 12 from sliding from the first end 232a toward the second end 232b along the flexible strand 214. Although the barbs 224 are shown on opposing sides of the flexible strand 214, the barbs 224 could be located on only one side of the flexible strand 214, spiral around an exterior surface of the flexible strand 214, or be in another configuration as long as the barbs 224 are angled toward the loop 215 on the first end 232a.

As shown in FIG. 4B, the loop 215 on the flexible strand 214 surrounded by the sheath 12 is placed near a mid-portion of the first piece of body tissue 28a with the penetrating pusher tool 34 (FIG. 2A). The sheath 12 next in line along the flexible strand 214 is then placed near a mid-portion of the second piece of body tissue 28b with the penetrating pusher tool 34 in a similar fashion. The remaining sheaths 12 on the flexible strand 214 are placed in an alternating pattern in the first and second pieces of body tissue 28a, 28b such that adjacent sheaths 12 are in alternating first and second pieces of body tissue 28a, 28b. Although five sheaths 12 are shown in the illustrated non-limiting embodiment, more or less than five sheaths 12 could be used to secure the first and second pieces of body tissue 28a, 28b together.

As shown in FIG. 4C, once all of the sheaths 12 have been lodged in the first and second pieces of body tissue 28a, 28b, the second end 232b of the flexible strand 214 is pulled in a direction P3 to tighten the first and second pieces of body tissue 28a, 28b together. Because the barbs 224 are angled toward the loop 215, the flexible strand 214 is able to be pulled through the first and second pieces of body tissue 28a, 28b in the direction P3. The barbs 224 prevent the flexible strand 214 from retracting back through the first and second pieces of body tissue 28a, 28b once pulled in the direction P3. Any excess flexible strand 214 can be trimmed so that the second end 232b of the flexible strand 214 would be flush with either the first or second pieces of body tissue 28a, 28b, if desired.

The anchor assembly of this disclosure provides an improved knotless technique to simplify and improve body tissue fixation. The barbs on the flexible strand grab and engage the sheaths with greater repeatability and provide stronger attachment to tissue than traditional sutures without barbs.

Although the different non-limiting embodiments are illustrated as having specific components, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should also be understood that although a particular component arrangement is disclosed and illustrated in these non-limiting embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A soft anchor assembly, comprising:
   at least one sheath; and
   a flexible strand passing through said at least one sheath, said flexible strand including:
   a first plurality of barbs that restrict movement of a first sheath of said at least one sheath in a first direction and allow movement of said first sheath in a second opposite direction; and
   a second plurality of barbs that restrict movement of a second sheath of said at least one sheath in said second direction and allow movement of said second sheath in said first direction.

2. The assembly as recited in claim 1, wherein said at least one sheath is a tubular sleeve made of a flexible material.

3. The assembly of claim 1, wherein said flexible strand includes a central region separating said first plurality of barbs from said second plurality of barbs and said first plurality of barbs and said second plurality of barbs are angled toward said central region.

4. The assembly of claim 1, wherein said first plurality of barbs are located adjacent a first end of said flexible strand and said second plurality of barbs are located adjacent a second opposite end of said flexible strand.

5. The assembly of claim 1, wherein said flexible strand forms a loop and includes a second plurality of barbs, said first plurality of barbs and said second plurality of barbs are threaded through said at least one sheath such that said first plurality of barbs overlap said second plurality of barbs within said at least one sheath.

6. The assembly of claim 1, wherein a first end of said flexible strand forms a loop at least partially surrounded by one of said at least one sheath.

7. The assembly of claim 6, wherein said first plurality of barbs extend from said loop to a second end of said flexible strand and are angled toward said loop.

8. The assembly of claim 6, wherein said at least one sheath includes a tubular body defining a bore and said flexible strand extends through said tubular body.

9. A method, comprising:
  attaching a first portion of body tissue to a second portion of body tissue, said attaching step including:
    utilizing a soft anchor assembly having a flexible strand passing through at least one sheath, said flexible strand having:
      a first plurality of barbs allowing movement of said at least one sheath along said flexible strand in a first direction and restricting movement of said at least one sheath in a second direction, wherein said first plurality of barbs allow said flexible strand to pass through said first portion of body tissue in a first direction and restrict said flexible strand from passing through said first portion of body tissue in a second direction; and
      a second plurality of barbs that allow said flexible strand to pass through said second portion of body tissue in said second direction and restrict said flexible strand from passing through said second portion of body tissue in said first direction;
  inserting one of said at least one sheath at least partially through the first portion of body tissue; and
  inserting another one of said at least one sheath at least partially through the second portion of body tissue.

10. The method of claim 9, wherein the first portion of body tissue and the second portion of body tissue are on opposite sides of a tear in a single piece of body tissue.

\* \* \* \* \*